US012702754B2

(12) United States Patent
Hooven et al.

(10) Patent No.: US 12,702,754 B2
(45) Date of Patent: Aug. 11, 2026

(54) MEDICAL FLUID INJECTION DEVICE WITH FILL INDICATOR

(71) Applicant: Enable Injections, Inc., Cincinnati, OH (US)

(72) Inventors: Michael D. Hooven, Cincinnati, OH (US); Matthew J. Huddleston, Loveland, OH (US); Joetta Renee Palmer, Mason, OH (US); David Stefanchik, Morrow, OH (US); Michael Lorenz, Cincinnati, OH (US)

(73) Assignee: Enable Injections, Inc., Cincinnati, OH (US)

( * ) Notice: Subject to any disclaimer, the term of this patent is extended or adjusted under 35 U.S.C. 154(b) by 1270 days.

(21) Appl. No.: 17/378,087

(22) Filed: Jul. 16, 2021

(65) Prior Publication Data

US 2021/0338928 A1 Nov. 4, 2021

Related U.S. Application Data

(63) Continuation-in-part of application No. 15/876,968, filed on Jan. 22, 2018, now abandoned.

(60) Provisional application No. 62/449,247, filed on Jan. 23, 2017.

(51) Int. Cl.

| | |
|---|---|
| ***A61M 5/14*** | (2006.01) |
| ***A61M 5/145*** | (2006.01) |
| *A61M 5/142* | (2006.01) |

(52) U.S. Cl.

CPC ..... *A61M 5/14593* (2013.01); *A61M 5/14248* (2013.01); *A61M 2205/3344* (2013.01); *A61M 2205/3386* (2013.01); *A61M 2205/502* (2013.01); *A61M 2205/583* (2013.01)

(58) Field of Classification Search

CPC .......... A61M 5/14244; A61M 5/14248; A61M 5/148; A61M 5/152; A61M 2005/14252; A61M 2005/14256; A61M 2005/1426; A61M 2005/14264; A61M 2005/3114; A61M 2005/3115; A61M 2005/3125; A61M 2005/3126; A61M 2005/31518; A61M 2205/58; A61M 2205/583

See application file for complete search history.

(56) References Cited

U.S. PATENT DOCUMENTS 4,140,117 A * 2/1979 Buckles ................ A61M 5/145 222/50

4,386,929 A * 6/1983 Peery .................... A61M 5/152 222/211

4,525,164 A * 6/1985 Loeb ..................... A61M 5/148 222/326

(Continued)

*Primary Examiner* — Kami A Bosworth

(74) *Attorney, Agent, or Firm* — Cook Alex Ltd.

(57) ABSTRACT

An injection device has a generally disc-shaped housing including an arcuate clear section and graduated markings or an arcuate droplet icon in an arcuate arrangement on or adjacent to the clear section. An arcuately expandable member is contained within the housing and is configured to hold a volume of liquid. An indicator is connected to the expandable member and positioned within the housing. The indicator is configured to move along an arcuate path adjacent to the clear section such that alignment of the indicator with the graduated markings or the arcuate droplet icon indicates a volume of liquid within the expandable member.

16 Claims, 7 Drawing Sheets

(56) References Cited

U.S. PATENT DOCUMENTS

| | | | | | |
|---|---|---|---|---|---|
| 4,601,707 | A * | 7/1986 | Albisser | A61M 5/148 604/151 |
| 4,685,902 | A * | 8/1987 | Edwards | A61M 5/1483 604/153 |
| 4,886,499 | A * | 12/1989 | Cirelli | A61M 5/142 604/141 |
| 5,848,990 | A * | 12/1998 | Cirelli | A61M 5/158 604/131 |
| 2011/0152762 | A1* | 6/2011 | Hershey | A61J 15/0042 604/100.02 |
| 2012/0310169 | A1* | 12/2012 | Sonderegger | A61M 5/14248 604/189 |
| 2013/0324884 | A1* | 12/2013 | Hadvary | A61M 5/1452 604/152 |
| 2015/0246176 | A1* | 9/2015 | Navarro | A61M 5/172 604/151 |
| 2015/0258286 | A1* | 9/2015 | Mosebach | A61M 5/326 604/111 |
| 2019/0117899 | A1* | 4/2019 | Byskov | A61M 5/31553 |

* cited by examiner

MEDICAL FLUID INJECTION DEVICE WITH FILL INDICATOR

CLAIM OF PRIORITY

This application is a continuation-in-part of U.S. patent application Ser. No. 15/876,968, filed Jan. 22, 2018, which claims the benefit of U.S. Provisional Application No. 62/449,247, filed Jan. 23, 2017, the contents of each of which are hereby incorporated by reference.

FIELD OF THE INVENTION

The present disclosure relates generally to devices for injecting medical fluids into patients and, in particular, to a medical fluid injection device with an indicator that displays the amount of medical fluid in the device.

BACKGROUND

Efforts have continued in recent years in the development of new and/or improved devices for transferring, reconstituting and/or injecting medical fluids, such as drugs, antibiotics, vaccines, biologics and other medicaments for therapeutic and/or diagnostic purposes. One example of such a development may be found in U.S. Pat. No. 9,925,333 to Hooven et al., owned by Enable Injections, Inc. of Cincinnati, Ohio, the contents of which are hereby incorporated by reference. That Hooven et al. '333 patent discloses a medical fluid injection device and an associated system or device for fluid transferring, mixing, diluting and/or reconstituting a medical fluid for injection. The injection device employs an internal reservoir in the form of a resilient balloon or bladder that expands arcuately as it is filled with medical fluid from the transfer device. Additional features may be found in U.S. patent Ser. No. 15/471,631, filed Mar. 28, 2017, the contents of which are hereby incorporated herein by reference.

The injection device of the Hooven et al. '333 patent may, after filling, be removed from the transfer device and placed on the skin of a patient and activated. Upon activation, an injection needle is advanced from the device into the skin of the patient and the inherent pressure provided by the expanded resilient reservoir forces the medical fluid through the needle and into the patient. As the medication is injected, the bladder deflates or contracts arcuately.

The injection device of the Hooven et al. '333 patent is particularly suited for injecting medical fluids. The device may include an adhesive surface so that it sticks to the patient's skin. It is desirable for the device to indicate to the user its status during different stages of use including, but not limited to, filling and delivery and completion of delivery.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto. In one aspect, an injection device features a generally disc-shaped housing including a top surface, a bottom surface, a dispensing port positioned in the bottom surface, an arcuate window and a fluid fill indicator in an arcuate arrangement on or adjacent to the arcuate window. The bottom surface is configured to be placed against a user's skin. An arcuately expandable member is contained within the housing and is configured to hold a volume of liquid. The expandable member includes an elastomeric bladder that is selectively in communication with the dispensing port. The elastomeric bladder has a distal end, is elongated and is configured to expand arcuately when filled with the volume of liquid and hold the volume of liquid under pressure with an elastic force in a wall of the elastomeric bladder so as to provide pressure to expel the liquid from the elastomeric bladder through the dispensing port as the elastomeric bladder contracts. An internal indicator is connected to the distal end of the elastomeric bladder. The internal indicator is positioned within the housing and configured to move along an arcuate path adjacent to and visible through the arcuate window as the elastomeric bladder expands and contracts.

DETAILED DESCRIPTION OF EMBODIMENTS

Figure 1A:
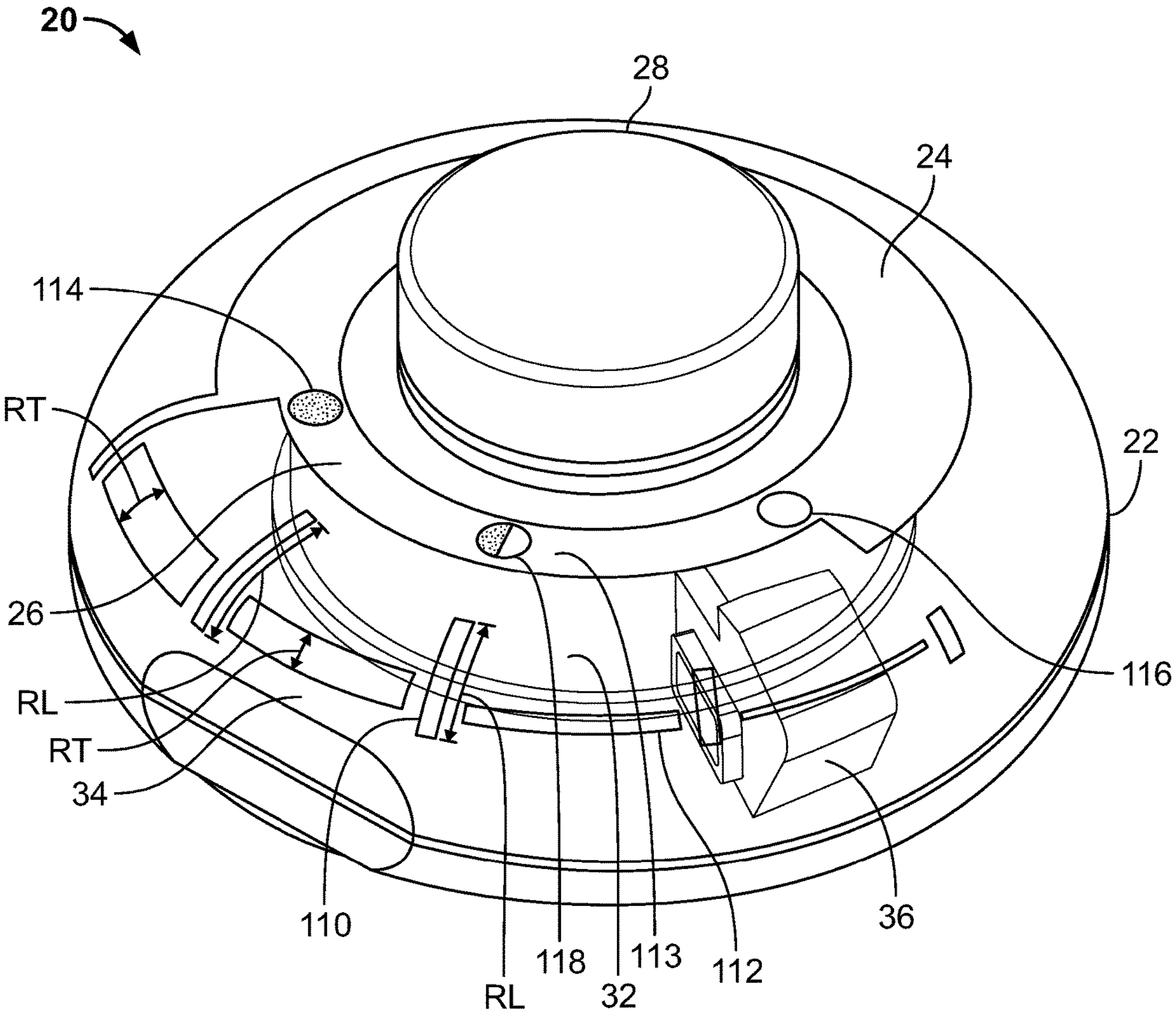
FIGS. 1A and 1B are top perspective views of a first embodiment of the medical fluid injection device with fill indicator in an empty and filled condition, respectively.
Figure 1B:
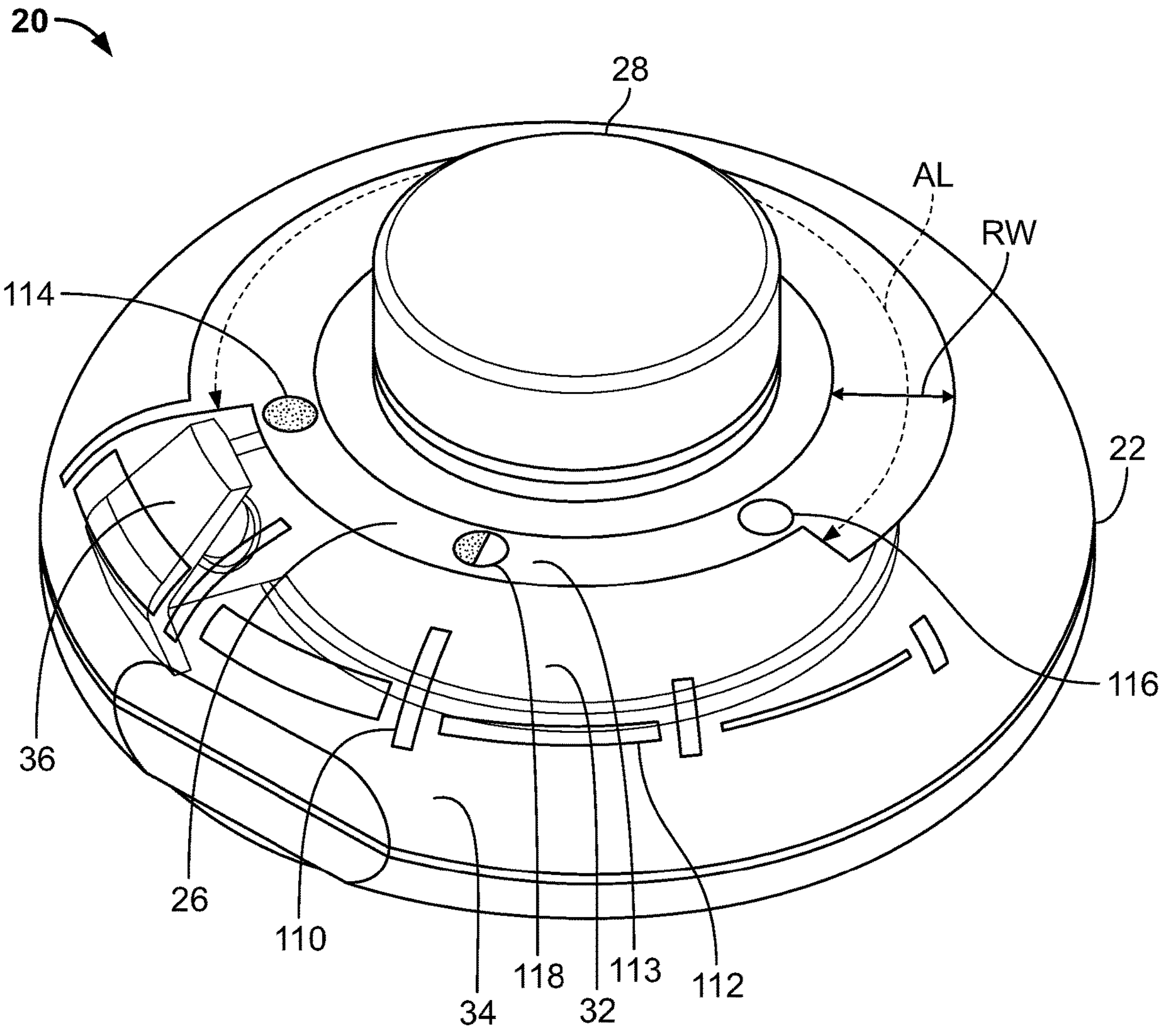

An embodiment of a medical fluid injection device is indicated in general at 20 in FIGS. 1A and 1B. The device includes a generally disc-shaped housing 22 that is preferably made in whole or in part of a transparent plastic material. A multi-function surface feature or aspect may be provided on or in association with the upper surface of the disc. For example, an arcuate shield 24, having a functionality to be explained below, may be located on or within the top surface of the housing, as is another feature, which may be in the form of a fluid fill indicator, such as a first graduated markings portion indicated generally at 26. The shield 24 and the first graduated markings portion 26 may cooperate to surround a button 28 that activates the device so that it provides an injection of a medical fluid to a user in the manner described below.

The fluid fill indicator may be of any suitable configuration, and "graduated marking(s)" as used herein is intended to refer generally to any suitable marking that visually indicates a fill level by a variation in graphical presentation, such as variation in length, width, size, shape, other, or different combination of such. When in the form of the first graduated markings portion 26, it may be positioned adjacent to a clear arcuate housing section or arcuate window 32. The illustrated housing is also provided with a second graduated markings portion 34 positioned on or adjacent to the clear arcuate section or arcuate window 32. While first and second graduated markings portions are illustrated, the device may be provided with only one graduated markings portion or more than two graduated markings portions.

The shield 24 and first and second graduated marking portions 26 and 34 may be provided in a number of ways. For example, the graduated markings 26 and 34 and shield 24 may be formed by a surface treatment on a portion of the housing, such as by a decal, sticker, paint, ink, surface finish or texture, embossing, raised surface or other surface finish or detail that provides a visual contrast with a remainder of the surface. The visual contrast may also be provided or formed by a material that provides a visual contrast with a remaining portion of the housing. This could include, for example, a material that is more or less opaque than the material of the surrounding portion of the housing or a material that features a color that differs from the material of the surrounding portion of the housing.

An internal indicator, referenced as 36 in FIGS. 1A and 1B, is visible through the clear arcuate section or arcuate window 32 of the housing and moves between a position (illustrated in FIG. 1A) that indicates the device is empty of medical fluid and a position (illustrated in FIG. 1B) that indicates that the device is full of medical fluid, and thus ready to be used to provide an injection.

Figure 2:
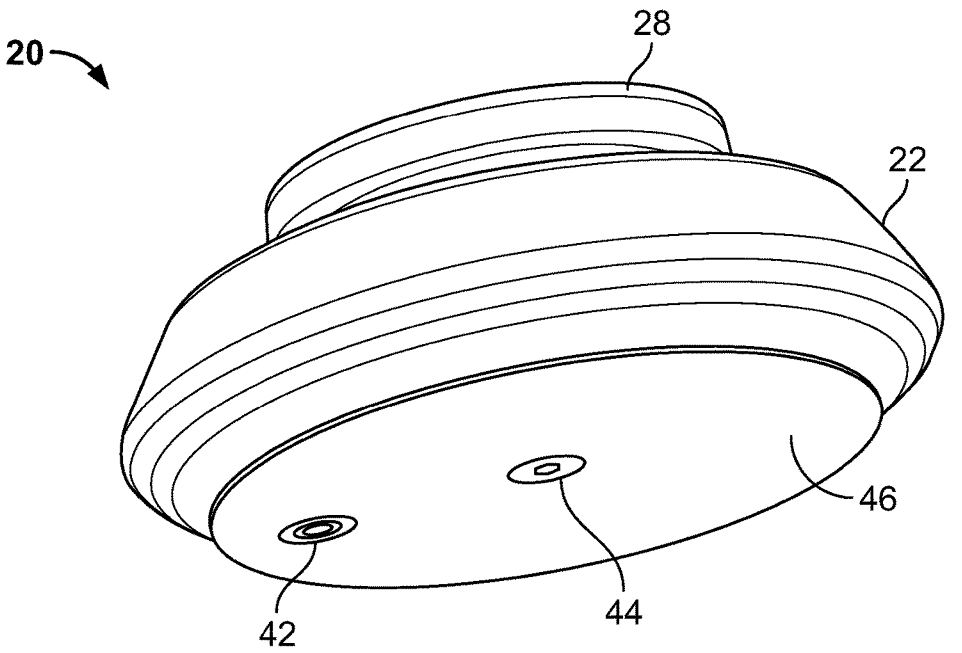
FIG. 2 is a bottom perspective view of the injection device of FIGS. 1A and 1B.
Figure 3:
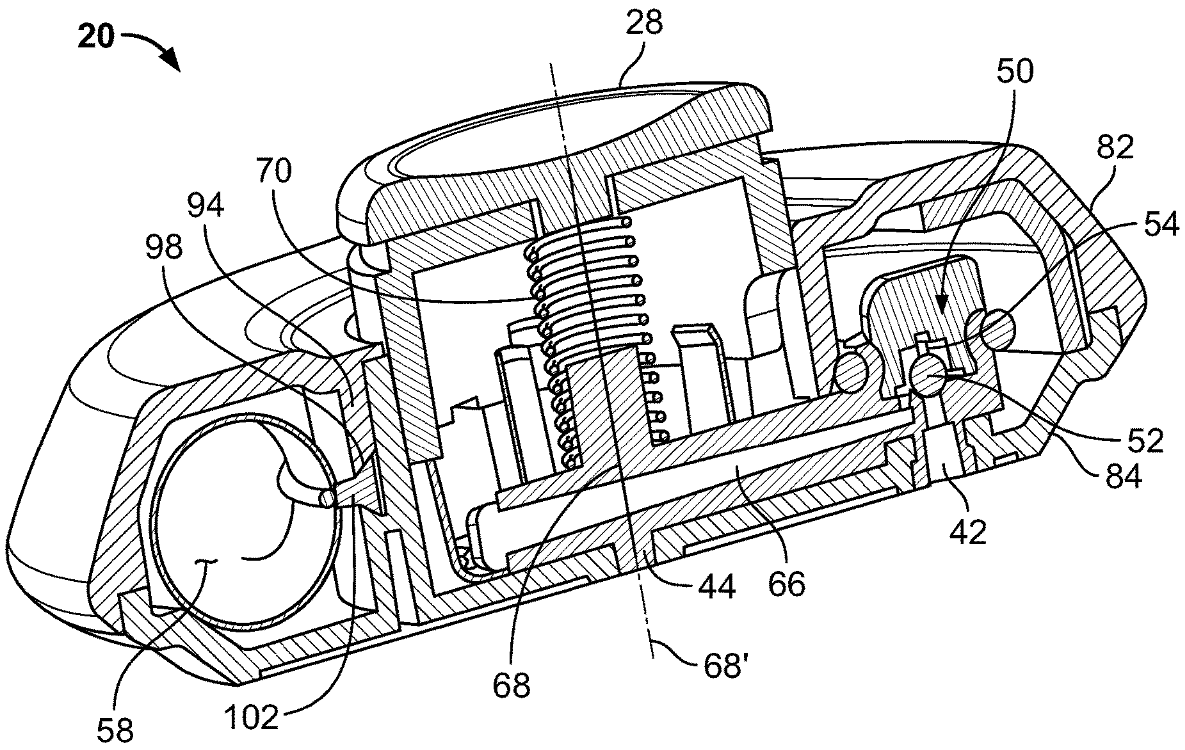
FIG. 3 is a cross sectional view of the injection device of FIGS. 1A-2.
Figure 5:
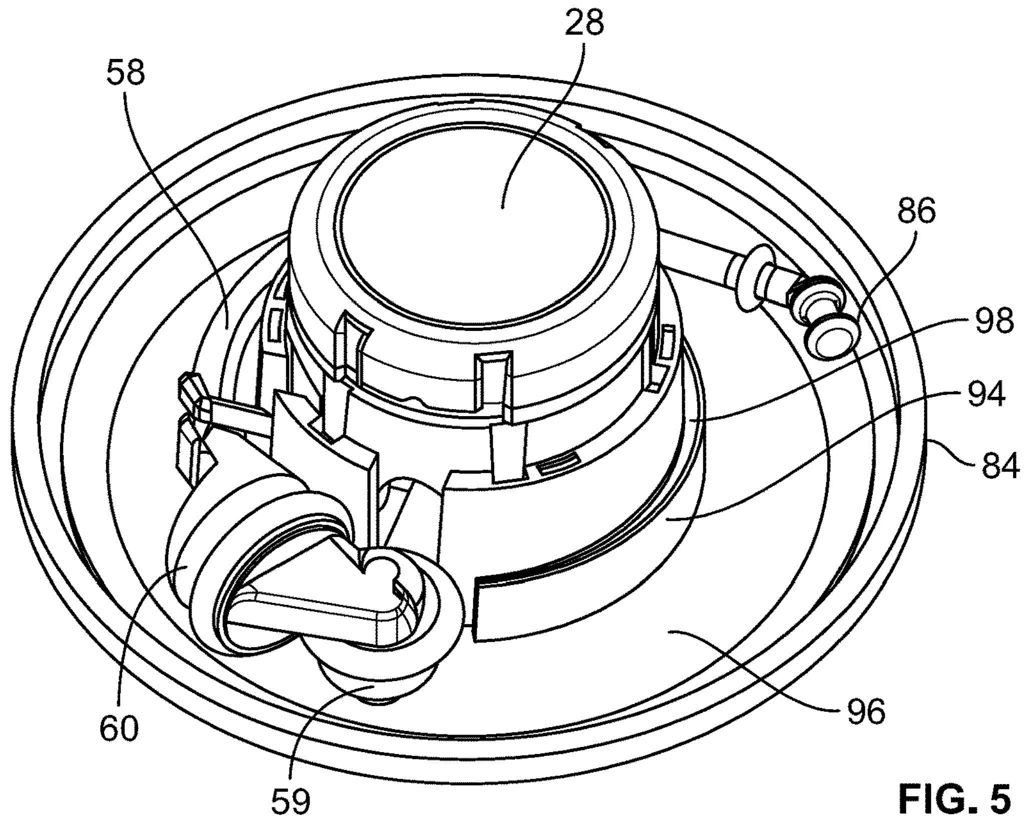
FIG. 5 is a top perspective view of the injection device of FIGS. 1A-4 with the expandable member empty and the dispense indicator, the indicator guide and the top portion of the housing omitted for clarity.
Figure 6:
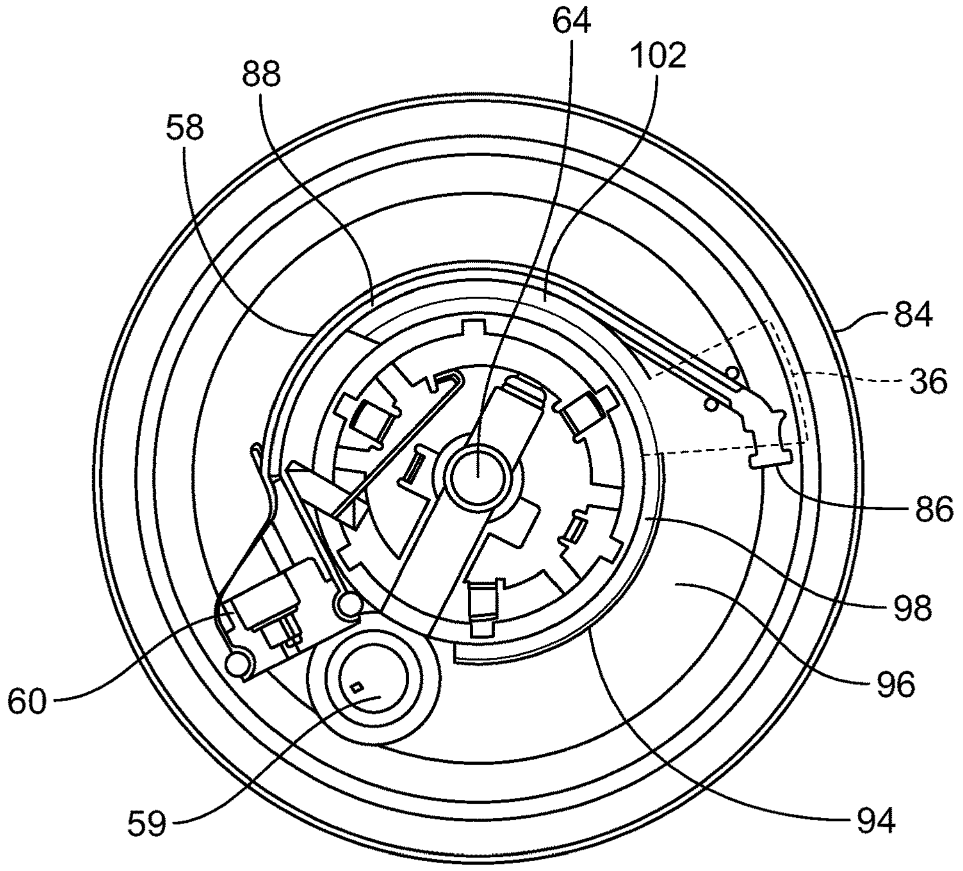
FIG. 6 is a top plan view of the injection device of FIG. 5.
Figure 7:
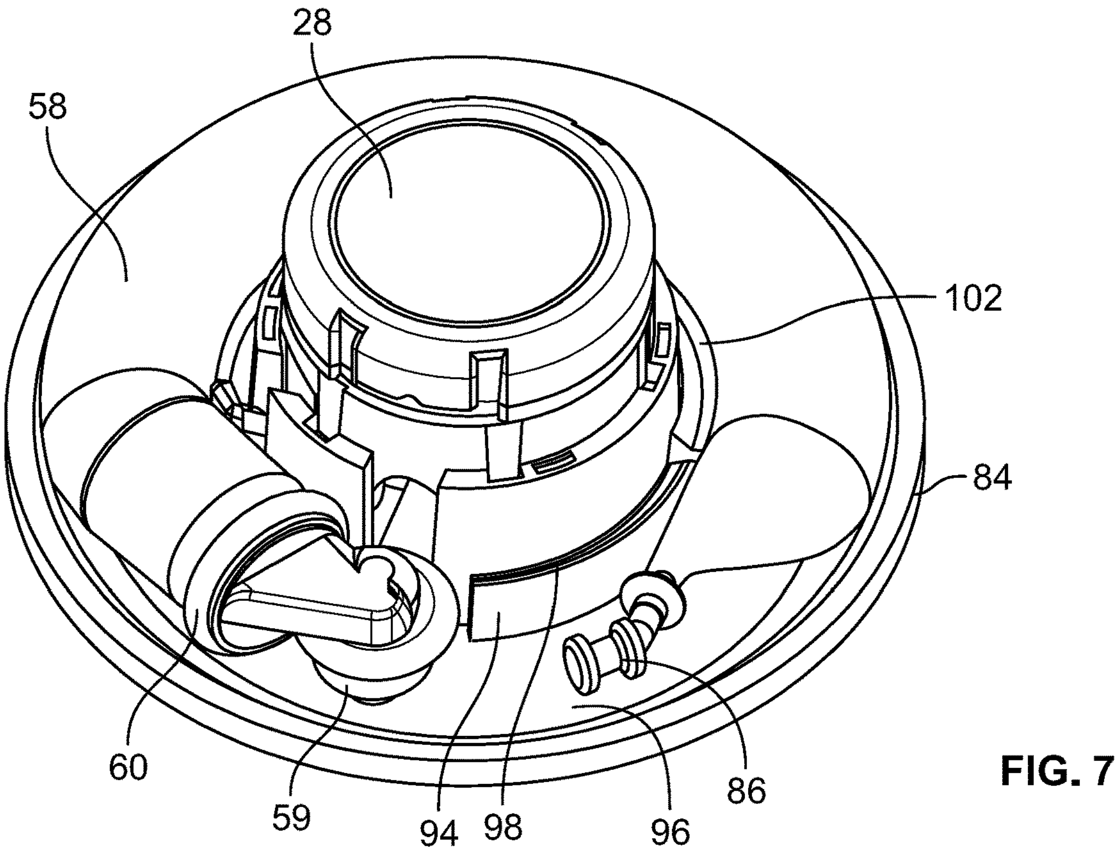
FIG. 7 is a top perspective view of the injection device of FIGS. 1A-6 with the expandable member filled with medical fluid and the dispense indicator, the indicator guide and the top portion of the housing removed for clarity.

As illustrated in FIG. 2, the bottom of the illustrated device is provided with a filling port 42 and a dispensing port 44. As described in the Hooven et al. '333 patent referenced previously, the device is filled with the medical fluid under pressure via a transfer device via the filling port 42. As will be described in greater detail below, the dispense port 44 contains a needle that, when extended from the bottom of the housing, injects the medical fluid into the patient/user. The bottom 46 of the device may be provided with an adhesive that permits the device to be secured to the patient's skin. As a result, the device may be concealed under the patient's clothing as the injection takes place As shown in FIG. 3, the filing port 42 is provided with a check valve, indicated in general at 50, such as a valve including a spherical valve member 52. As described in the Hooven et al. '333 patent referenced previously, the check valve permits medical fluid to flow from the transfer device through the filling port 42 and into a fluid cavity 54 (FIG. 3) of a manifold, indicated in general at 56 in FIG. 4, so that an expandable member, indicated at 58 in FIGS. 3, 5 and 6, is filled with the fluid. As an example only, the expandable member may be an elastomeric bladder or balloon.

Figure 4:
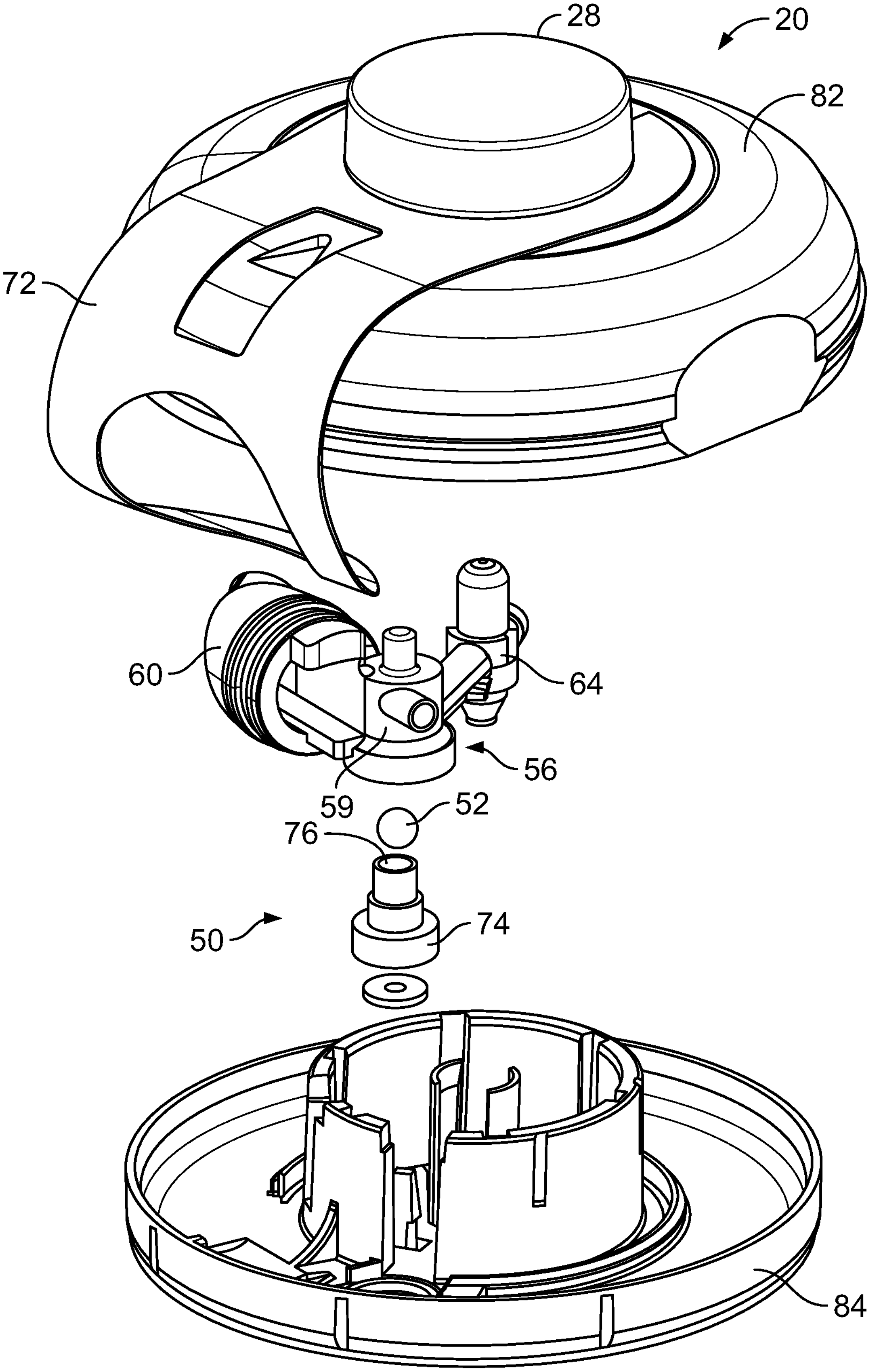
FIG. 4 is an exploded view of the injection device of FIGS. 1A-3 with the bladder and needle omitted.

More specifically, with reference to FIG. 4, the manifold 56 as illustrated includes a valve housing 59 and a first branch containing a fluid flow passage that leads to a mounting member 60. As illustrated in FIG. 5, the expandable member 58 is attached to the mounting member 60.

The manifold 56 of FIG. 4 also includes a second branch that leads to a needle housing 64. The second branch includes a fluid flow path 66 (FIG. 3). The needle housing (64 of FIG. 4) contains a needle (68 of FIG. 3) having a side opening that leads to the lumen of the needle. This side opening is positioned so as to be in fluid communication with fluid flow path 66 when the needle is moved in the extended deployed position, indicated in phantom in FIG. 3 at 68', by the patient pushing button 28, against the urging of coil compression spring 70. As illustrated in FIG. 4, a safety tab 72 may be provided to block actuation of the button 28 of the device to prevent accidental deployment of the needle, and may be easily removed when the device is to be used.

As shown in FIG. 4, an elastomeric valve body 74 features a fluid flow lumen 76 which receives the spherical valve member 52. The valve body 74 is positioned within the valve housing 59 so that the fluid cavity 54 (FIG. 3) is defined. The valve member 52 is sized so as to circumferentially engage the inner surface of the sidewall, and an annular shoulder portion formed therein, of the valve body 74 when the valve member is positioned within the fluid flow lumen 76 and a pressurized medical fluid is not being provided to the filling port 42 by the transfer device.

When the pressurized medical fluid is provided via a transfer device to the check valve 50 via the filling port, the fluid flows through the fluid flow lumen 76 of the elastomeric valve body 74. As a result, the spherical valve member 52 is lifted off of the annular shoulder of the fluid flow lumen and the sidewall of the fluid flow lumen radially expands away from the valve member 52 so that the fluid may flow through the first branch of the manifold 56, the mounting member 60 and into the expandable member 58 (of FIGS. 5-8). While some of the fluid may enter the fluid flow passage 66 (FIG. 3), the amount is not significant and it does not leak out of the device as the side opening of the needle 68 is not in alignment with the fluid flow passage 66. A more detailed description of the illustrated valve may be found in U.S. Pat. No. 11,033,680, filed Jun. 8, 2016, the contents of which are hereby incorporated by reference herein.

When the filling of the expandable member is completed, the injection device is removed from the transfer device, and the check valve 50 prevents the fluid within the expandable member from being forced out of the filling port.

With reference to FIG. 3, when the button 28 is pressed, after the bottom surface of the device is placed on the patient's skin, the side opening of the needle, when in the position illustrated at 68', is positioned so as to be in fluid communication with fluid flow path 66. As a result, the expandable member 58 forces the medical fluid therein under pressure through the manifold (56 in FIG. 4), into the fluid flow path 66 and into and through the lumen of the needle 68' into the patient.

As shown in FIGS. 3 and 4, the housing of the injection device may include a top portion 82 and a bottom portion 84. The top and bottom portions may be secured together by adhesive, heat or radio frequency welding, mechanical interconnections or any other fastening arrangement known in the art.

With reference to FIGS. 5-8, the expandable member 58 is provided with a distal end 86, which may include a downstream air remover or filter to allow for venting of trapped air during filling. An internal mandrel 88 may be connected to distal end 86 of the expandable member 78. The mandrel 88 could include a slot along its length that is in communication with the downstream air remover or filter to aid in the venting of air during the filling process.

As illustrated in FIGS. 5 and 6, the mandrel 88 also preferably pre-stresses the expandable member 58 to a slightly expanded position when it is unfilled, so that when the expandable member expels the medical fluid, it will contract or collapse to a condition where it is still stretched or stressed and continues to exert pressure on any fluid there within. This better assures that all or substantially all of the medical fluid is fully expelled from the injection device. Additionally, the expandable member 58 could be flattened/stretched by 'wrapping' it around a surface within the injection device, such as a cylindrical wall 94 (FIGS. 3 and 5). In the illustrated embodiment, the cylindrical wall 94 is formed by the top and bottom portions 82 and 84 of the injection device housing. The pre-stress created in the expandable member 58 would act to eliminate any residual fluid volume remaining within.

As noted previously, the expandable member 58 may be an elastomeric balloon or bladder. The material composition of expandable member 58 may preferably be silicone. Alternatively, the material composition of the expandable member 58 may be a blend of different materials including but not limited to bromobutyl, chlorobutyl, isoprene, polyisoprene, SBR, polybudtadiene, EPDM, natural rubber and silicone. Alternatively, the expandable member 58 may be made from a thermoplastic elastomer. In addition, as explained in greater detail in the Hooven et al. '333 patent referenced previously, the expandable member 58 may be coated to improve surface properties.

Because the expandable member 58 receives the medical fluid under pressure during filling, it enlarges and the resilience creates a pressure which tends to expel the medical fluid. Introducing the medical fluid into the expandable member under pressure causes it to stretch and expand both in diameter and length. The volume range of the injection device may be, as an example only, 0.5 to 50 milliliters.

As previously mentioned, and illustrated in FIGS. 3-8, the injection device includes a disc-shaped housing that includes a bottom portion 84. As illustrated in FIGS. 5-8, the interior surface of the bottom portion has an arcuate slot or recess 96 formed therein. The expandable member 58 rests in the recess, with the proximal end for communicating directly or indirectly with the injection needle (68 of FIG. 3) through the manifold (56 of FIG. 4), as explained previously. The expandable member 58 expands and contracts lengthwise within the arcuate recess 96.

Figure 8:
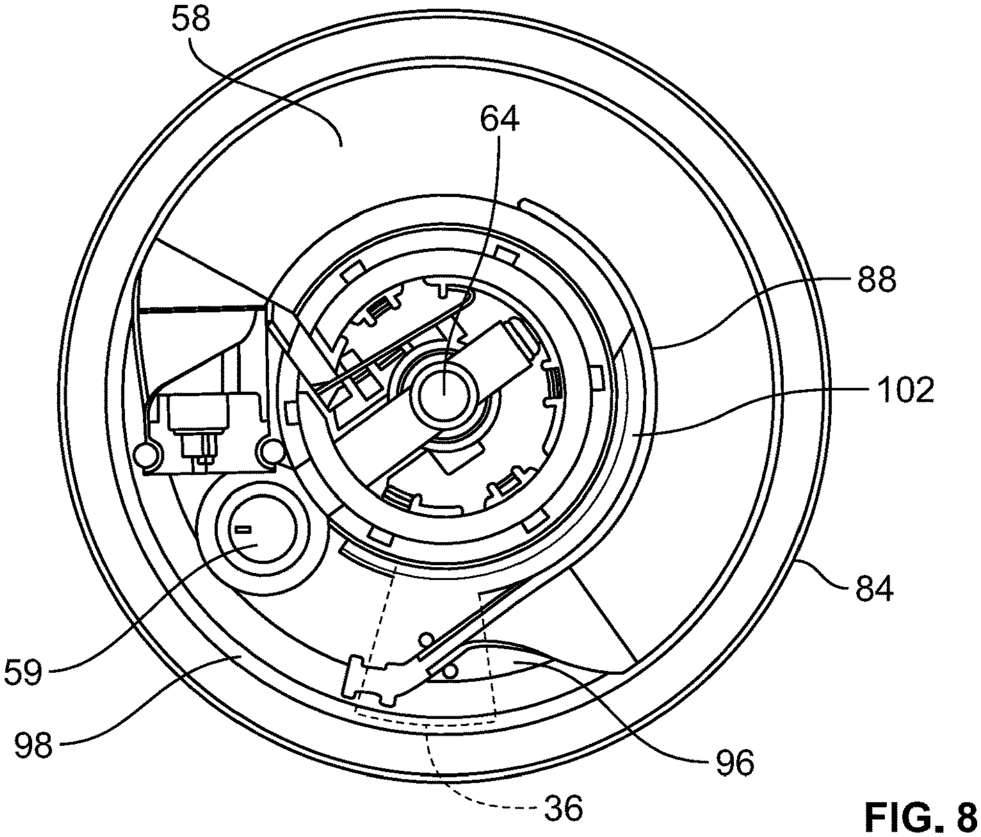
FIG. 8 is a top plan view of the injection device of FIG. 7.

With reference to FIGS. 3, and 6-8, an arcuate guide path or track 98, for example, one having a dovetail cross section, may be formed in the cylindrical sidewall 94 of the housing and an indicator guide 102 is positioned within the track in a sliding fashion. As illustrated in FIG. 3, the indicator guide 102 is attached to the inner portion of the expandable member 58. As a result, the indicator guide traverses a portion of the arcuate guide path 98 as the expandable member arcuately transitions between the unfilled and filled conditions. As illustrated in FIGS. 6 and 8, the dispense indicator 36 is attached to the indicator guide 102. As a result, the dispense indicator 36 travels along a path defined by a portion of the arcuate recess 96 as the expandable member 58 transitions between the empty/unfilled condition in FIGS. 1A, 5 and 6 and in the filled condition in FIGS. 1B, 7 and 8. The indicator guide 102 may be integrally molded with the dispense indicator 36 or it may be a separate component that is joined to the dispense indicator either directly or indirectly (such as through both components being individually joined to the distal end 86).

Returning back to FIGS. 1A and 1B, the graduated markings may include a plurality of lines 110 spaced along the path of the indicator, with each line being oriented generally radially relative to a center of the disc-shaped injection device and substantially perpendicular to the path of the indicator 36. As is clear from FIGS. 1A and 1B, the lines decrease in radial length (RL) from a first length at a location on the housing (illustrated in FIG. 1B) corresponding to a position of the indicator when the expandable member (58 of FIGS. 3 and 5-8) is filled with liquid to a second length at a location on the housing (illustrated in FIG. 1A) corresponding to a position of the indicator when the expandable member is substantially empty of liquid.

The graduated markings may also include a number of lines 112 spaced along the path of the indicator with each line being oriented substantially parallel to the path of the indicator. As shown in FIGS. 1A and 1B, the lines 112 decrease in radial thickness (RT) from a first thickness at a location on the housing (illustrated in FIG. 1B) corresponding to a position of the indicator when the expandable member is substantially filled with liquid to a second thickness at a location on the housing (illustrated in FIG. 1A) corresponding to a position of the indicator when the expandable member is substantially empty of liquid.

As noted previously, the graduated markings may also include a portion 26 that includes a number of circles spaced along the path of the indicator. The circles include a first circle 114, which fully contains a fill color indicia and is located on the housing corresponding to a position of the indicator when the expandable member is substantially filled with liquid. The circles also include a second circle 116, which lacks any of the fill color indicia and is located on the housing corresponding to a position of the indicator when the expandable member is substantially empty of liquid. The graduated markings may further include one or more intermediate circles, such as intermediate circle 118 half filled with the fill color indicia and located on the housing corresponding to a position of the indicator when the expandable member is substantially half full of liquid. While three circles are illustrated, an alternative number of indicia having the same or different shapes or configurations may be used.

As noted previously, the housing may also include an arcuate shield portion 24. The arcuate shield portion 24 is preferably positioned and sized (both radially and lengthwise) to substantially conceal the expandable member (58 of FIGS. 3 and 5-8) when it is empty. The radial width (RW) and annular length (AL) of the shield are seen in FIGS. 1A and 1B. In addition, the shield portion 24 may provide space or background for a trademark, product name, user information and warnings, and any other text or graphics to be displayed. Furthermore, the top of the button 28 may have a surface treatment comparable to the shield 24 and/or the graduated markings 26 and 28 that may also be used for this purpose.

The shield and graduated markings may be of a same color that contrasts with a color of the housing, and the button of the device may include a button color treatment of the same color as the shield and the graduated markings. Furthermore, the housing may be made of a substantially clear plastic with the shield and graduated markings featuring a contrasting color or finish to enhance visibility.

Figure 9:
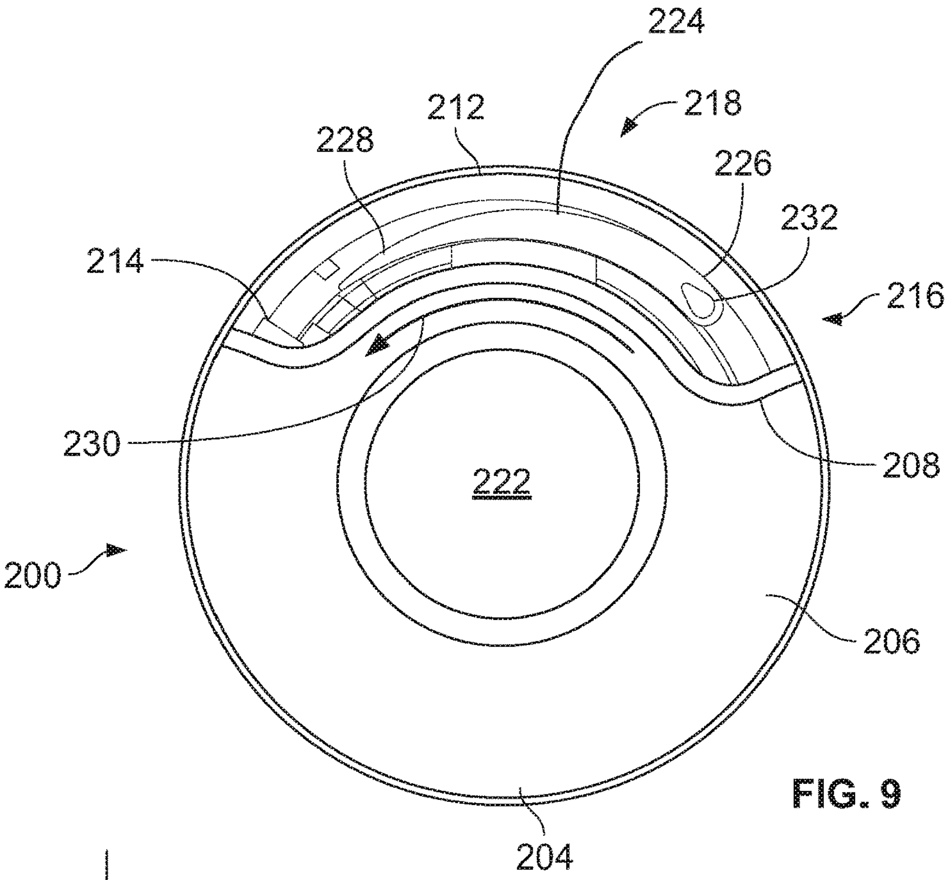
FIG. 9 is a top plan view of a second embodiment of the injection device of the disclosure.
Figure 10:
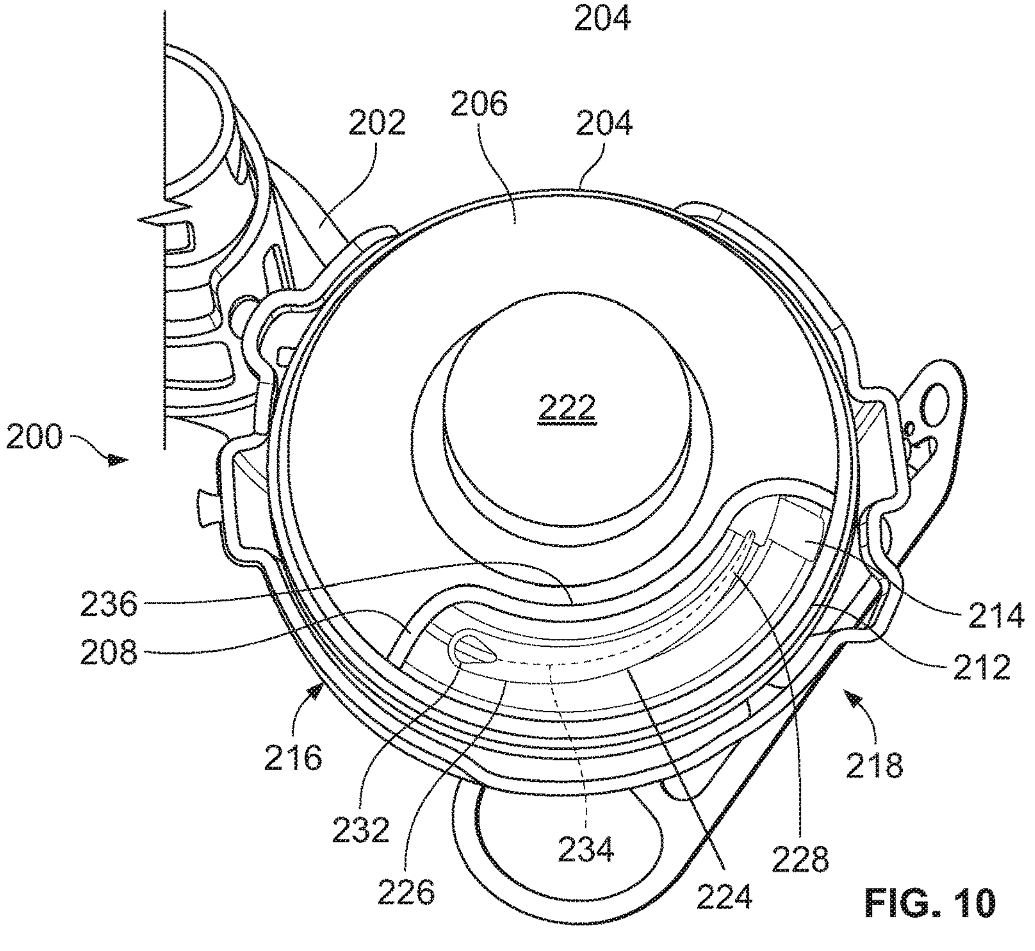
FIG. 10 is a perspective view of the injection device of FIG. 9 mounted on a medical fluid transfer device.

An alternative embodiment of the injection device of the disclosure is indicated in general at 200 in FIGS. 9 and 10. In FIG. 10, the injection device is mounted on a medical fluid transfer device, indicated at 202, which may be used to transfer liquid medication to the injection device 200. An example of a suitable medical transfer device is disclosed in commonly assigned U.S. patent application Ser. No. 16/755,786, filed Apr. 13, 2020, and U.S. Provisional Application No. 63/060,924, filed Aug. 4, 2020, the contents of each of which are hereby incorporated by reference.

The injection device of FIGS. 9 and 10 may be structurally and operationally the same as the device described with reference to FIGS. 1-8. As illustrated in FIGS. 9 and 10, the injection device 200 includes a generally disc-shaped housing 204 that is preferably made in whole or in part of a transparent plastic material. An arcuate shield portion 206 is located on or within the top surface of the housing and is preferably positioned and sized (both radially and lengthwise), as in previous embodiments, to substantially conceal the expandable member (58 of FIGS. 3 and 5-8) when it is empty. In addition, the shield portion 206 may provide space or background for a trademark, product name, user information and warnings, and any other text or graphics to be displayed.

The injection device of FIGS. 9 and 10 also includes a frame 208 bordering at least one side of, and preferably surrounding, an arcuate clear section or window 212. As in the previous embodiments, an internal indicator 214 is visible through the arcuate window 212 and between a position (illustrated in FIGS. 9 and 10) that indicates the device is empty of medical fluid and a position (illustrated by arrow 216 in FIGS. 9 and 10) that indicates that the device is full of medical fluid, and thus ready to be used to provide an injection.

The frame 208 preferably includes a color that contrasts with the color of the shield portion 206 so as to guide a user's eye or draw a user's attention to the arcuate window 212 where the position of the internal indicator 214 may be viewed. As an example only, the frame may be colored red while the shield portion may be white. The frame 208 also provides the user with an indication that the injection device should be mounted in a position whereby the arcuate window 212 may be viewed.

In addition, the injection device 200 includes a fluid fill indicator, indicated generally at 218 in FIGS. 9 and 10. The shield portion 206, the frame 208 and the arcuate window 212 may cooperate to surround a button 222 that, when pressed, activates the device so that it provides an injection of a medical fluid to a user in the manner described above for previous embodiments.

With continued reference to FIGS. 9 and 10, the fluid fill indicator 218 includes an arcuate tear or droplet shaped icon, indicated in general at 224, having an enlarged head portion 226 and a tapered tail portion 228. The head portion 224 optionally includes a tear or droplet shaped icon window 232. In alternative embodiments, the icon window 232 may be omitted, or a number of icon windows may be provided in different sizes along the droplet icon 224. The icon window(s) may also alternatively be round or any other desired shape. The droplet icon 224 features an arcuate centerline, illustrated in phantom at 234 in FIG. 10, with a curvature that is preferably generally parallel with the curvature of the top portion 236 (FIG. 10) of the frame 208. The head portion 226 of the droplet icon 224 is positioned over or adjacent to the position 16 of the internal indicator 214 when the injection device is full while the end of the tail portion 228 is over or adjacent to the position of the internal indicator 214 illustrated in FIGS. 9 and 10 when the injection device is empty or nearly empty. The droplet icon therefore decreases in thickness in the direction of travel (indicated by arrow 230 in FIG. 9) of the internal indicator 214 as the injection device dispenses medication. In other words, the arcuate droplet icon oriented so that the internal indicator moves in a first direction from the tapered tail portion towards the enlarged head portion as the elastomeric bladder expands and the internal indicator moves in a second direction from the head portion and towards the tail portion, and opposite the first direction, as the elastomeric bladder contracts. The position of the internal indicator 214 along the droplet icon 224 therefore provides a user with an indication of the fill level of the injection device.

As illustrated in FIGS. 9 and 10, the droplet icon 224 is preferably positioned on the arcuate window 212 of the injection device. In alternative embodiments, the droplet icon 224 could be positioned adjacent to the arcuate window 212, such as between the frame 208 and button 222.

The shield 206, frame 208 and/or droplet icon 224 may be provided on the disc-shaped housing 204 in a number of ways. For example, they may be formed by a surface treatment on a portion of the housing, such as by a decal, sticker, paint, ink, surface finish or texture, embossing, raised surface or other surface finish or detail that provides a visual contrast with a remainder of the surface. The visual contrast may also be provided or formed by a material that provides a visual contrast with a remaining portion of the housing. This could include, for example, a material that is more or less opaque than the material of the surrounding portion of the housing or a material that features a color that differs from the material of the surrounding portion of the housing.

The droplet icon 224 communicates a gradual process of filling/emptying of the injection device 200 rather than metered increments in a manner that is simple and quick to read. The droplet icon 224 also conveys the direction of travel of the internal indicator 214 as it travels empty to full and full to empty and an estimated injection device fill level.

While the preferred embodiments of the disclosure have been shown and described, it will be apparent to those skilled in the art that changes and modifications may be made therein without departing from the spirit of the disclosure, the scope of which is defined by the following claims.

What is claimed is:

1. An injection device comprising:

a. a disc-shaped housing including a top surface, a bottom surface, a dispensing port positioned in the bottom surface, an arcuate window and a fluid fill indicator in an arcuate arrangement on the arcuate window, wherein the bottom surface is configured to be placed against a user's skin;

b. an arcuately expandable member contained within said disc-shaped housing configured to hold a volume of liquid, said expandable member including an elastomeric bladder that is selectively in communication with the dispensing port, has a distal end, is elongated and is configured to expand arcuately when filled with the volume of liquid and hold the volume of liquid under pressure with an elastic force in a wall of the elastomeric bladder so as to provide pressure to expel the liquid from the elastomeric bladder through the dispensing port as the elastomeric bladder contracts;

C. an internal indicator connected to the distal end of the elastomeric bladder, said internal indicator positioned within the disc-shaped housing and configured to move along an arcuate path adjacent to and visible through the arcuate window as the elastomeric bladder expands and contracts;

d. wherein the fluid fill indicator includes an arcuate droplet icon positioned on the arcuate window of the disc-shaped housing and having an enlarged head portion and a tapered tail portion, said arcuate droplet icon being more opaque than the arcuate window and oriented so that the internal indicator moves in a first direction from the tapered tail portion towards the enlarged head portion as the elastomeric bladder expands and the internal indicator moves in a second direction from the head portion and towards the tail portion, and opposite the first direction, as the elastomeric bladder contracts.

2. The injection device of claim 1 further comprising a guide path formed on an inner surface of the disc-shaped housing, said guide path configured to hold the internal indicator in a sliding fashion so that the internal indicator is constrained to follow the guide path as a length of the expandable member changes.

3. The injection device of claim 2 wherein the guide path includes a track and the internal indicator includes an indicator guide that is positioned within the track in a sliding fashion.

4. The injection device of claim 1 wherein the arcuate droplet icon includes an icon window positioned within the enlarged head portion.

5. The injection device of claim 4 wherein the icon window is droplet-shaped.

6. The injection device of claim 1 further comprising an arcuate shield positioned on the top surface of the disc-shaped housing, said arcuate shield configured to substantially conceal the expandable member when empty.

7. The injection device of claim 6 further comprising a frame bordering at least one side of the arcuate window of the disc-shaped housing, said frame having a frame color that contrasts with a shield color of the arcuate shield.

8. The injection device of claim 7 wherein at least a portion of the frame is arcuate and the arcuate droplet icon features an arcuate centerline having a curvature that is parallel with a curvature of the arcuate portion of the frame.

9. The injection device of claim 1 further comprising a liquid injection needle having a lumen selectively in fluid communication with the expandable member.

10. The injection device of claim 9 further comprising a user-activated button configured to move the liquid injection needle from a first position, where the lumen is not in fluid communication with the expandable member, to a second position where the lumen is in fluid communication with the expandable member.

11. The injection device of claim 10 wherein the liquid injection needle is positioned entirely within the disc-shaped housing when in the first position and the liquid injection needle is partially extended out of the disc-shaped housing when in the second position.

12. The injection device of claim 10 further comprising a spring engaging the user-activated button and the disc-shaped housing so as to urge the user-activated button into a position corresponding to the first position of the liquid injection needle.

13. The injection device of claim 10 wherein the user-activated button centrally extends through the top surface of the disc-shaped housing and the disc-shaped housing includes an arcuate shield positioned on the top surface to substantially conceal the expandable member when empty.

14. The injection device of claim 10 further comprising a shield, wherein the user-activated button includes a button color treatment of the same color as the shield.

15. The injection device of claim 14 wherein the disc-shaped housing is substantially formed of clear plastic with the shield positioned on the clear plastic.

16. The injection device of claim 1 wherein the disc-shaped housing includes a filling port and wherein said filling port and said dispensing port are separate and distinct from one another and selectively in fluid communication with the elastomeric bladder.

* * * * *